United States Patent
Kierath et al.

(10) Patent No.: US 8,137,261 B2
(45) Date of Patent: Mar. 20, 2012

(54) DEVICE FOR THE TREATMENT OF OBESITY

(75) Inventors: Tony Kierath, West Perth (AU); Walter Egle, Koblach (AT)

(73) Assignee: A.M.I. Agency for Medical Innovations GmbH, Feldkirch (AT)

( * ) Notice: Subject to any disclaimer, the term of this patent is extended or adjusted under 35 U.S.C. 154(b) by 650 days.

(21) Appl. No.: 12/379,293

(22) Filed: Feb. 18, 2009

(65) Prior Publication Data
US 2009/0157107 A1 Jun. 18, 2009

Related U.S. Application Data

(63) Continuation of application No. PCT/AT2007/000334, filed on Jul. 4, 2007.

(30) Foreign Application Priority Data

Aug. 21, 2006 (AT) .................................. A 1394/2006

(51) Int. Cl.
*A61F 13/00* (2006.01)
*A61B 17/08* (2006.01)
(52) U.S. Cl. .......................................... 600/37; 606/151
(58) Field of Classification Search ............... 600/29–32, 600/37; 128/DIG. 25; 606/151–158, 213, 606/217, 228; 604/909
See application file for complete search history.

(56) References Cited

U.S. PATENT DOCUMENTS

| 2004/0158272 | A1 | 8/2004 | Hofle et al. |
| 2004/0260316 | A1 | 12/2004 | Knudson et al. |
| 2004/0260319 | A1 | 12/2004 | Egle |
| 2004/0267377 | A1 | 12/2004 | Egle |
| 2009/0062824 | A1* | 3/2009 | Berg et al. ...................... 606/157 |
| 2009/0240268 | A1* | 9/2009 | Kassab et al. .................. 606/157 |

FOREIGN PATENT DOCUMENTS

| EP | 0 702 529 | 10/2002 |
| EP | 1 669 045 | 6/2006 |
| WO | 02/053040 | 7/2002 |

OTHER PUBLICATIONS

International Search Report issued Dec. 7, 2007 in the International (PCT) Application.

* cited by examiner

*Primary Examiner* — John Lacyk
(74) *Attorney, Agent, or Firm* — Wenderoth, Lind & Ponack, L.L.P.

(57) ABSTRACT

A device for the treatment of obesity includes at least one first and one second band each with closure means for closing the particular band to form a ring. The first band is connected or is connectable with an enveloping part and is placeable about the esophagus, the stomach or a transition region between the esophagus and the stomach. The second band, also connected or connectable with the enveloping part, is placeable about the stomach distally to the first band and spaced apart from it, and the region of the stomach located between the first and the second band is envelopable by the enveloping part.

19 Claims, 4 Drawing Sheets

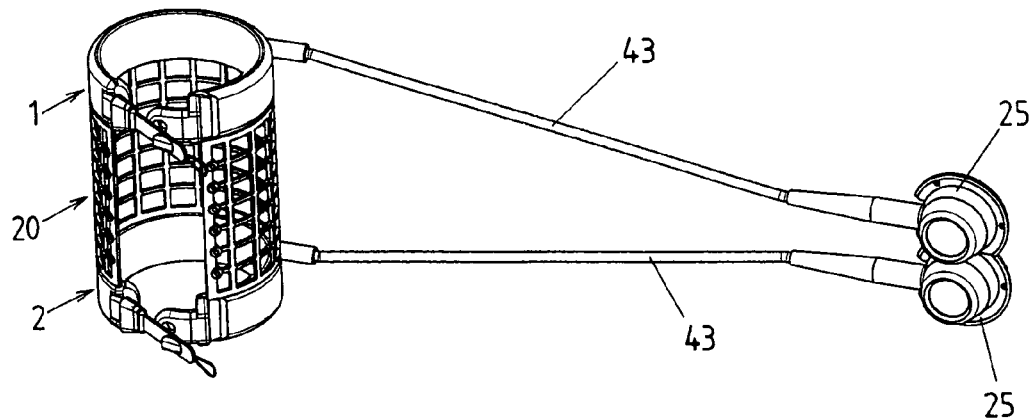
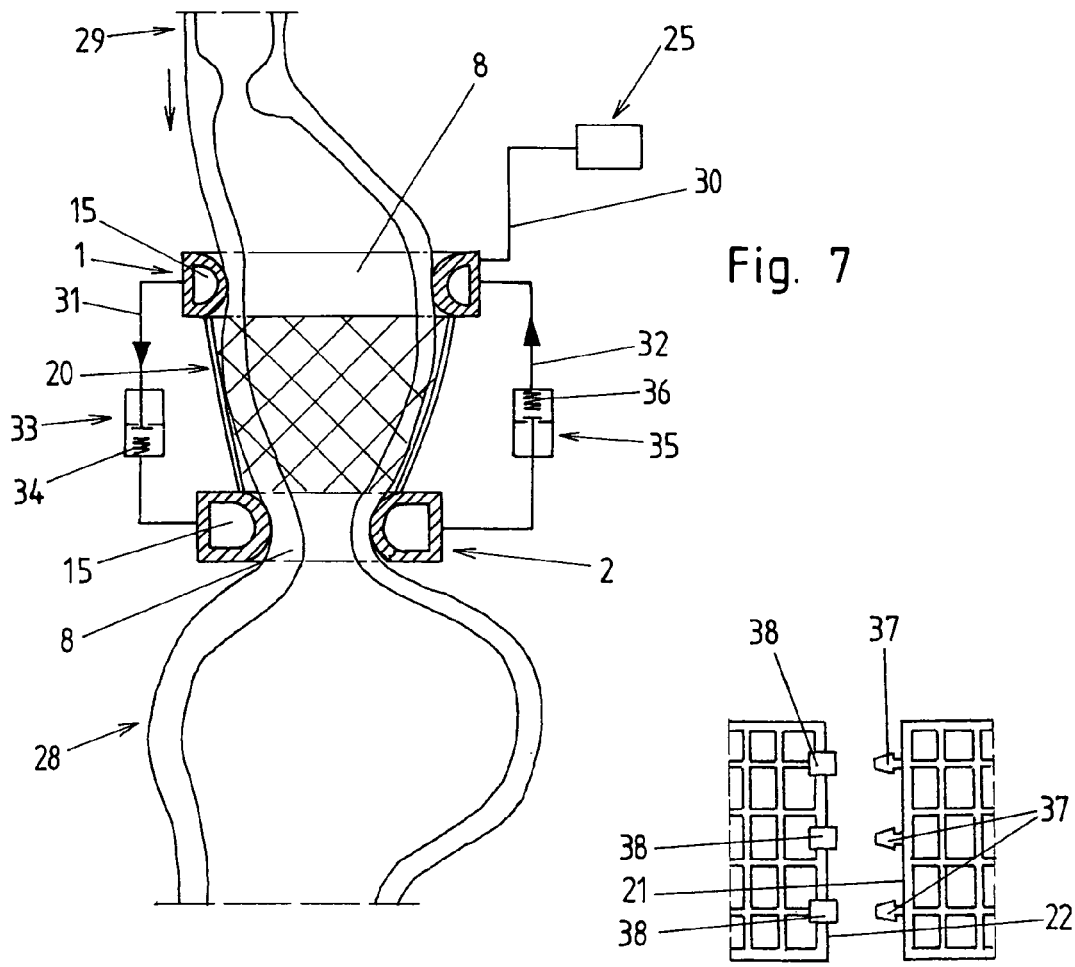

DEVICE FOR THE TREATMENT OF OBESITY

This application is a continuation of International Application No. PCT/AT2007/000334, filed Jul. 4, 2007, the entire disclosure of which is incorporated herein by reference.

BACKGROUND OF THE INVENTION a) Field of the Invention

The invention relates to a device for the treatment of obesity comprising a band annularly placeable about the stomach with closure means for closing the band to form a ring and an enveloping part connected or connectable with the band for enveloping a gastric region adjoining the applied band.

b) Description of Related Prior Art

Devices for treating obesity by means of a band annularly placeable about the stomach, which band is closable by closure means to form a ring, are known in various implementations and are most frequently referred to as gastric bands. Such a gastric band is disclosed, for example in EP 0 702 529 B1. The band, which can be placed annularly about the stomach, includes a longitudinally extending inner hollow chamber and at the two ends of the band first and second closure parts are disposed, which can be latched in position with one another to close the band. To constrict the passage cross section of the gastric band opening of the closed gastric band, the hollow chamber is filled with the desired quantity of filler medium. This filling takes place through an injection port connected with the gastric band via a tubule, which port is subcutaneously implanted in the patient. Further gastric bands with adjustable passage cross section are disclosed, for example, in US 2004/0158272 A1, US 2004/0260319 A1 and US 2004/0267377 A1.

Gastric bands are conventionally wrapped about the stomach in the proximity of the inlet of the esophagus. If a gastric band is placed further down, the gastric reservoir remaining above the band is relatively large and the stomach, moreover, can become dilated in this region such that the desired weight loss is not attained. If the stomach is constricted, as is customary, far above in the proximity of the inlet of the esophagus, the food taken in by the patient can only slowly pass through this constricted region. It is therefore possible for the ingested nourishment to accumulate in the region of the distal esophagus. Contrary to its natural function, the distal esophagus is consequently utilized as a reservoir for food. A possible long-term complication is the development of a dilatation of the distal esophagus, upon the occurrence of which the gastric band must be removed.

A gastric band of the above described type is disclosed in EP 1 669 045 A1. To prevent expansion of a gastric region proximal to the gastric band, an enveloping part is fastened on the band, which part projects laterally in the proximal direction. After implantation of the band, the enveloping part encompasses a gastric region proximal to the gastric band in the manner of a collar and elastically supports the gastric wall enveloped by it.

SUMMARY OF THE INVENTION

The invention addresses the problem of providing an improved device of the above described type, in which the stomach can be utilized as a reservoir organ and which has high effectiveness.

According to the invention this is attained through a device for the treatment of obesity comprising a first band annularly placeable about the stomach with closure means for closing the band to form a ring, a second band annularly placeable about the stomach with closure means for closing the band to form a ring, and an enveloping part connected or connectable with the first and second band, wherein the first band, connected or connectable with the enveloping part, can be placed about the esophagus, the stomach or a transition region between the esophagus and the stomach and the second band, also connected or connectable with the enveloping part, can be placed distally of the first band, and spaced apart from it, about the stomach and the gastric region located between the first and the second band is envelopable by the enveloping part.

Through the invention, consequently, a gastric band of at least stages is provided. The first and the second band closed to form a ring represent each a brake for the food and the enveloping part, located between the first and the second band and encompassing the stomach in the manner of a collar, acts counter to and limits a dilatation of the stomach in the region between the first and the second band. Thereby an effective deceleration of the food ingested by the patient with the fast onset of the sensation of being satisfied can be attained, wherein, nevertheless, the stomach in the region between the second and the first band can be utilized as a reservoir.

The first band can be applied, for example, about the proximal stomach in the proximity of the esophageal inlet in order to form a first brake for the swallowed food. The second band, applied distally to this first band, can advantageously have an inner diameter which, compared to the first band is smaller or it can be adjusted to such small inner diameter in order to form a narrower constriction compared to the first band.

In an advantageous embodiment of the invention only this first and second band are provided. In a further embodiment of the invention a further third band, applicable distally to the second band, can be provided, wherein the region of the stomach between the third and the second band is enveped by the enveloping part or by a further enveloping part extending between the second and the third band. Thereby a further brake stage or a further usable gastric reservoir can be provided between the third band and the second band. Further bands, each with interspaced enveloped sections of the stomach, are also conceivable and feasible.

In a preferred embodiment of the invention the first and the second band and the enveloping part connected with the first and the second band are formed by the manufacturer as a prefabricated unit, the parts of which unit are connected with one another. This prefabricated unit is implantable as a whole into the body of the patient. The enveloping part is herein preferably nondetachably connected with the first and second band, i.e. it cannot be removed without destroying the prefabricated unit. Due to the implementation as a prefabricated unit, a simple and reliable implantation is attained, wherein the risk of operative errors is reduced. The enveloping part can, for example, be adhered on the first and second bands. The integral formation in one piece of the enveloping part with the first and/or the second band or portions thereof is also conceivable and feasible.

On the other hand, it is also conceivable and feasible to connect the enveloping part with the first and/or second band via closure elements which, on the one hand, are disposed on the enveloping part and, on the other hand, on the first and/or second band, for example in the form of closure elements which can be latched into position with one another. The connection of the enveloping part with the first and/or second band could in this case also be carried out only during the implantation of the device. It would further be conceivable and feasible to suture the enveloping part to the first and/or second band in the process of implantation.

It is preferred that the inner diameter of the first and second band is adjustable after these are closed to form a ring. For this purpose the first and second band each have preferably at least one inner hollow chamber fillable with a filler medium, which chamber extends in the longitudinal direction of the band at least over a large portion of its length. The inner diameter of the band can herein be regulated through the quantity of the introduced filler medium, as is sufficiently known in gastric bands. It would also be conceivable and feasible, for example, to regulate the inner diameter of the first and/or the second band through a piston-cylinder unit acting between the longitudinal ends of the band, as is also already known.

Further advantages and details of the invention will be explained in the following in conjunction with the enclosed drawing.

BRIEF DESCRIPTION OF THE DRAWINGS

In the drawings:

FIG. 5 and FIG. 6 are oblique views of minimally modified embodiments of the invention, FIG. 7 is a schematic sectional representation of a device applied about the stomach according to a further embodiment variant of the invention, FIG. 8 is a view of a section of the enveloping part according to a further variant of the invention, FIG. 9 and FIG. 10 an embodiment of a three-stage gastric band according to the invention in the opened and closed state of the bands, in oblique view.

DETAILED DESCRIPTION OF THE INVENTION

Figure 1:
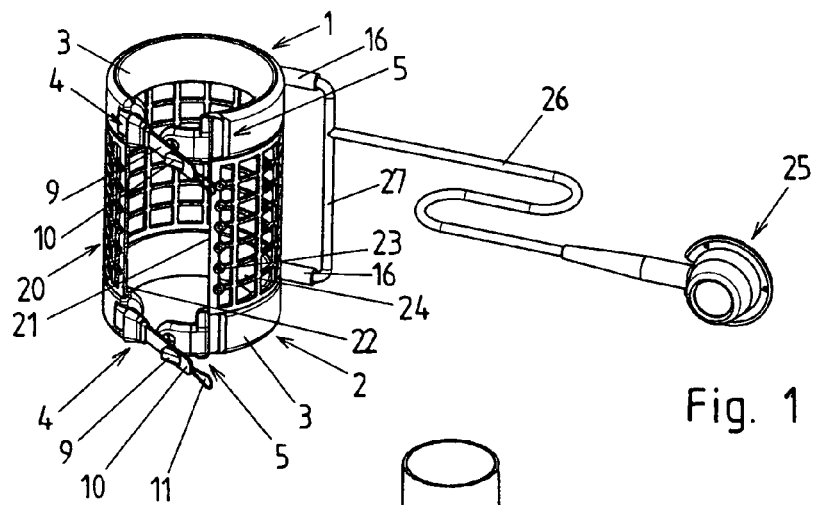
FIG. 1 is a first embodiment of the invention in the opened state of the first and second band, in oblique view.

A first embodiment example of the invention is depicted in FIG. 1 to 4. The device according to the invention comprises in this embodiment example a first and a second band 1, 2, which are formed in the same manner, wherein parts of the first and second band 1, 2 are denoted by the same reference numbers. A particular band 1, 2 comprises a body section 3, at both ends of which a first and a second closure part 4, 5 are disposed. The first closure part 4 comprises an extension 6 with a latch projection 7. At the end remote from the body section 3 of the first closure part 4 is disposed a draw tab 9 with a prelatch projection 10 and a suspension loop 11.

The second closure part 5 includes an eye-shaped section 12, on which a draw tab 13 is disposed.

Figure 3:
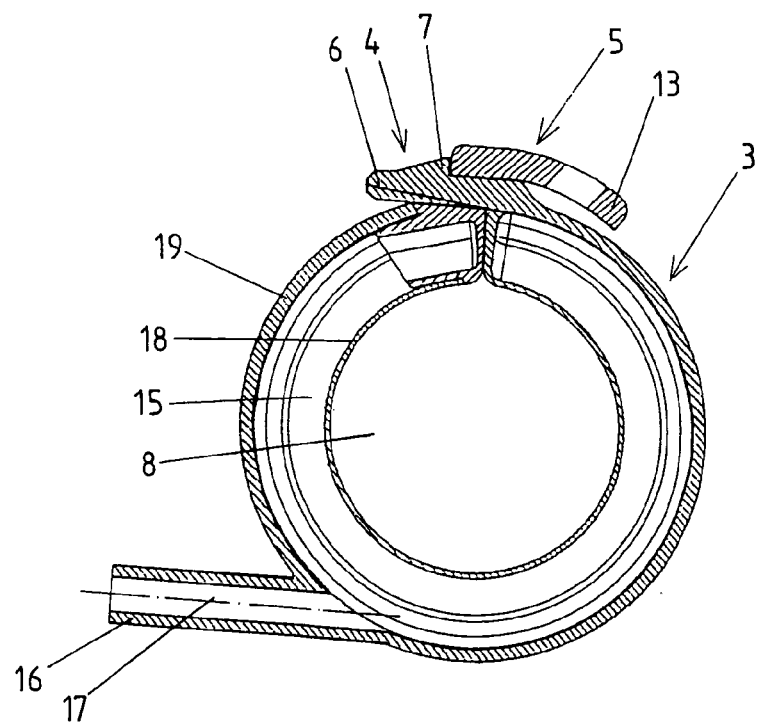
FIG. 3 is a longitudinal section through one of the two bands (wherein the draw tab of the first closure part has been cut off)
Figure 4:
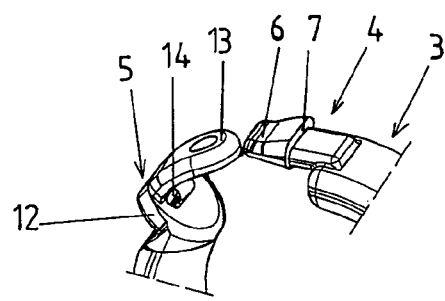
FIG. 4 is an oblique view of the end sections of one of the two bands with the closure parts in the opened state of the band (without the draw tab of the first closure part for the sake of clarity)

To close the particular band 1, 2 to form a ring with a passage opening 8, the first closure part 4 is pulled through the opening 14 of the eye-shaped section 12 of the second closure part 5 until the latch projection 7 latches in position. The prelatch projection 10 facilitates the closing of the gastric band thereby that after the draw tab 9 has been pulled through the opening 14 until the latching-in of the prelatch projection 10 a partially closed state is provided. After the band 1, 2, has been closed, the draw tab 9 can be cut off, as is shown in FIG. 3.

The closure means for closing the particular band 1, 2 can be modified in various ways.

The body section 3 of a particular band 1, 2 includes an inner hollow chamber 15 continuous over its length. The body section 3 is herein formed by a tube-like element, which at both of its ends is closed by adhered-in closures, on which the closure parts 4, 5 are disposed. The body section 3 is further provided with a connection tubule 16, whose inner channel 17 communicates with the hollow chamber 15 of the body section 3.

In the depicted embodiment example the connection tubule 16 is disposed on the body section 3 in a region remote from the closure parts 4, 5. It would also be conceivable and feasible for the connection tubule 16 to extend, for example, through the first closure part 4, as is known.

The passage openings 8 of the bands 1, 2 closed to form rings are preferably disposed coaxially with respect to one another (in the relaxed state of the device).

When the inner hollow chamber 15 is filled through the connection tubule 16 with a filler medium, for example sterile water or X-ray contrast agents, the inner diameter of the band 1, 2 closed to form a ring, can be varied as is also known. Herein the inner wall 18 of the body section 3 expands with the decrease of the diameter of the passage opening 8 of the band 1, 2, closed to form a ring, in the direction toward the central longitudinal axis of the ring. The inner wall 18 herein has a greater elasticity than the outer wall 19 of the body section 3, which can be reinforced, for example, by a fabric interfacing.

The bands 1, 2 are preferably comprised, at least substantially, of silicon, thus for example with the exception of fabric interfacing.

The device comprises further an enveloping part 20. This part extends between the bands 1, 2 spaced apart from one another. The enveloping part 20 is herein connected with the particular band 1, 2 substantially over the length of each particular band 1, 2 (over the length of the band except for the closure parts 4, 5) or over the length of the body section 3 of each particular band. In the depicted embodiment example it is here adhered on the bands 1, 2 on their side margins facing one another.

After the bands 1, 2 have been closed to form rings, the circumferential ends 21, 22 of the enveloping part 20 are located adjacent to one another. These circumferential ends 21, 22 are provided with suture eyelets 23 through which they can be sutured to one another.

The sections of the enveloping part 20 adjoining the circumferential ends 21, 22 could, instead, also overlap one another in the closed state of bands 1, 2.

The enveloping part 20 is preferably comprised of silicon. It can be implemented such that it is elastic. It is also conceivable and feasible to embed reinforcement material, in particular reinforcement fibers, into the silicon.

In the embodiment example according to FIG. 1 to 4 the enveloping part 20 is implemented in the manner of a meshing or netting, wherein it has a multiplicity of penetration openings 24 distributed over its extent.

In the embodiment example according to FIG. 1 to 4 the bands 1, 2 are fillable via a common injection port 25, wherein the injection port 25 is connected via connection tubules 26, 27 with the connection tubules 16 of bands 1, 2.

Figure 2:
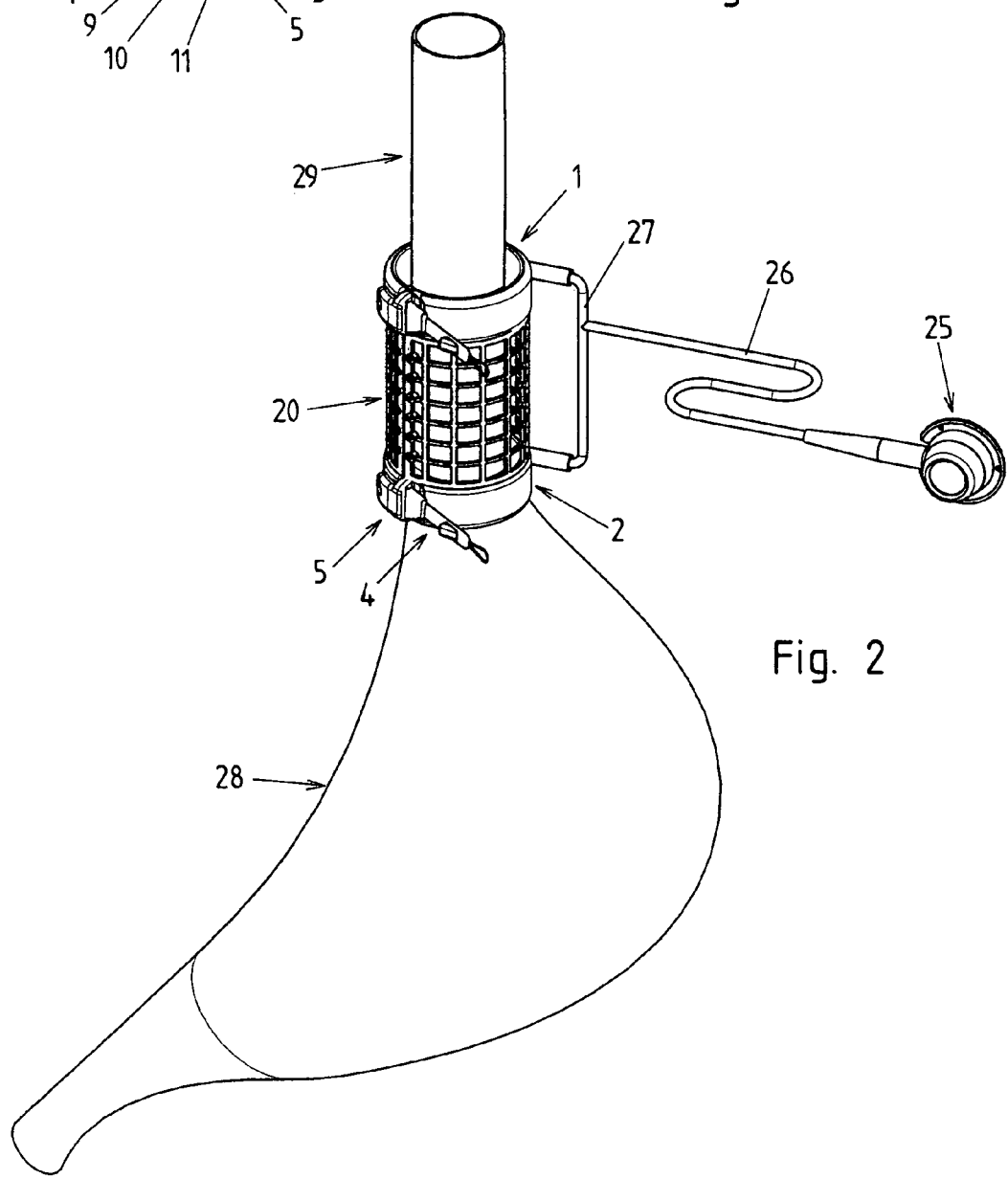
FIG. 2 is a schematic diagram of the device applied about the stomach.

The implanted state of the device is depicted schematically in FIG. 2. The first band 1 is applied about the stomach 28 in the proximity of the inlet of the esophagus 29 or about the esophagus 29 in the proximity of its inlet into the stomach 28 or in the transition region between esophagus 29 and stomach 28. The second band 2 is applied about the stomach 28 further distally, i.e. further removed from the cardiac orifice of the stomach. The region of the stomach 28 located between the first and second band 1, 2 is enveloped by the enveloping part 20. The circumferential ends 21, 22 of the enveloping part 20 are preferably sutured to one another through the suture eyelets 23, which is not shown in FIG. 2 for the sake of clarity. The bands 1, 2 are further filled with the desired quantity of filler medium in order to adjust the passage openings 8 of bands 1, 2 to the desired size. The filling in this embodiment example is carried out through a common injection port 25 and the passage openings 8 of bands 1, 2 are adjusted jointly while coupled with one another.

The passage opening 8 of the second band 2 is preferably smaller than that of the first band 1. This can be attained, for example, thereby that the body section 3 of the second band 2 is shorter than that of the first band 1. The inner wall 18 of the second band 2 could, instead, also be implemented such that it is more readily expandable than the inner wall 18 of the first band 1, for example by means of different material thicknesses and/or different materials. A combination of these measures is also feasible. Swallowed food can thereby pass through the first band 1 more easily than through the second band 2.

Since the inner hollow chamber 15 of bands 1, 2 communicate with one another via the connection tubule 27, moreover, a pressure increase occurs in the second band 2 when a bolus is pressed through the passage opening 8 of the first band 1, such that the passage opening 8 of the second band 2 becomes constricted. The food is thereby more strongly decelerated by the second band. If, on the other hand, food is pressed through the second band 2, the pressure in the first band 1 increases whereby the immediate follow-on of the supply of food is decelerated.

Overall a two-stage braking of supplied food occurs until it reaches the main region of the stomach located below the second band 2. The speed at which the food can be supplied is thereby decreased. Through the nourishment accumulating in the region between the second band 2 and the first band 1, further, the patient experiences the sensation of being satisfied.

The region of the stomach 28 located between the second band 2 and the first band 1 can be utilized as a reservoir for food which has passed through the first band 1, not, however, through the second band 2. Through the enveloping part 20 a dilatation of this gastric region is herein prevented or limited.

Figure 5:
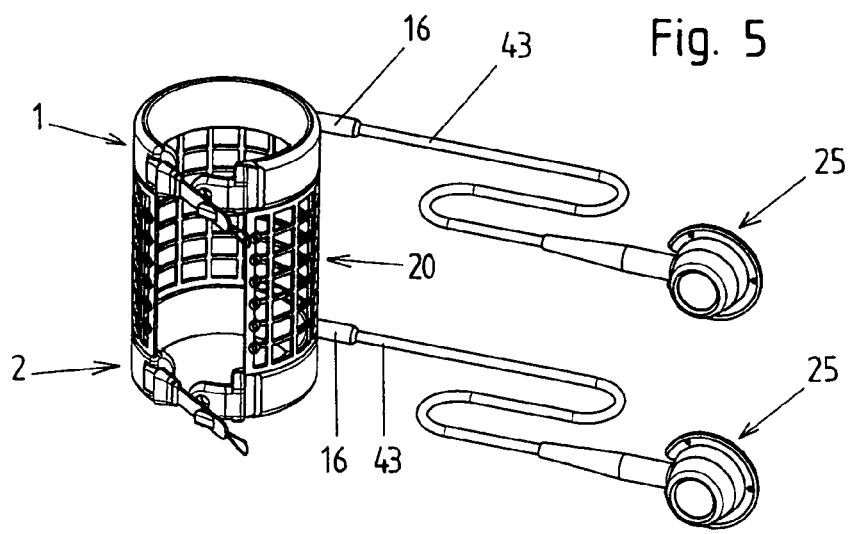

The embodiment depicted in FIG. 5 corresponds to the previously described embodiment example except that for each band 1, 2 a separate injection port 25 is provided, which is connected with the hollow chamber 15 of a particular band via a connection tubule 43, wherein the hollow chambers 15 of the two bands 1, 2 also do not communicate with one another. The passage openings 8 of bands 1, 2 can thus be adjusted independently of one another. The two injection ports 25 can, if desired, be implanted at different sites in the body in order to permit simple differentiation for the treating physician.

The embodiment example according to FIG. 6 only differs from the embodiment example depicted in FIG. 5 thereby that the two injection ports 25 are connected to form a unit.

In FIG. 7 is schematically depicted a further embodiment example in the implanted state. This embodiment example corresponds to the embodiment explained in conjunction with FIG. 1 to 4 with the following differences: the injection port 25 communicates via a connection tubule 30 with the inner hollow chamber 15 of the first band 1. The inner hollow chambers 15 of the first and of the second band 1, 2 are connected with one another through first and second connection ducts 31, 32. In the first connection duct 31 a check valve 33 is disposed, which is opened in the presence of a flow from the first band 1 in the direction to the second band 2 when a closure force F1 is exceeded. A spring element 34 effecting this closure force is drawn schematically in the Figure. In the connection duct 32 a check vale 35 is disposed, which is opened in the presence of a flow from the second band 2 in the direction toward the first band 1 when a closure force F2 is overcome. A spring element 36 effecting this closure force F2 is again indicated schematically.

The closure force F1 is less than the closure force F2. Bands 1, 2 can be implemented in the same manner, thus have the same length and the same elasticity of their inner walls 18. On the other hand, the lengths of bands 1, 2 and/or the elasticities of the inner walls 18 can also differ.

When food is being pressed through the passage opening 8 of the first band 1 and herein so large a pressure increase of the filler medium occurs that the closure force F1 is exceeded, the filler medium can flow from the first band 1 into the second band 2, whereby its passage opening 8 is decreased. When the quantity of food between the first band 1 and the second band 2 increases, the pressure in the hollow chamber 15 of the second band 2 increases until lastly the closure force F2 of the check valve 35 is exceeded. As a consequence, filler medium can flow from the second band 2 to the first band 1 whereby the passage opening 8 of the second band 2 is enlarged and that of the first band 1 is reduced. For the patient the supply of further food through the first band 1 is therewith made more difficult until the quantity of food in the reservoir between the first and the second band 1, 2 has decreased again.

To close the enveloping part 20 to form a circumferentially closed collar, in a further embodiment of the invention closure means can be provided, for example in the form of a latch closure shown schematically in FIG. 8. On one circumferential end 21 first closure elements 37 with latch projections are provided which can be inserted into eye-shaped second closure elements 38 on the second circumferential end 22 and be latched in position with them.

Figure 9:
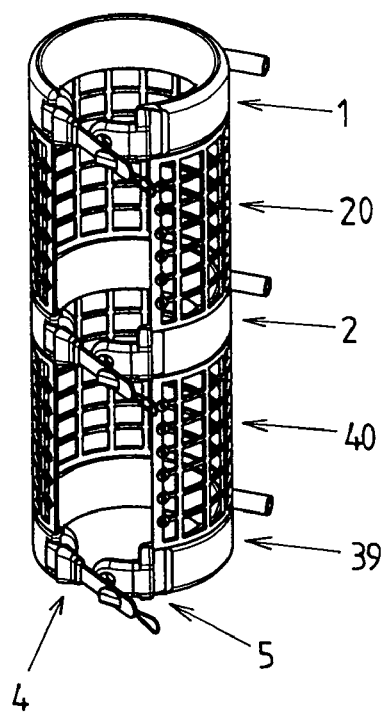
Figure 10:
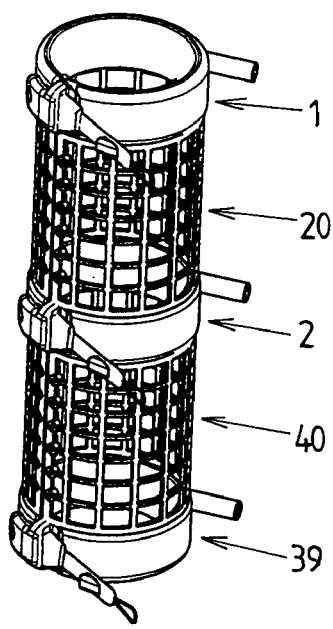

The further embodiment example depicted in FIGS. 9 and 10 differs from the previously described embodiment examples thereby that a third band 39 and a second enveloping part 40 are provided, wherein the device is preferably again implemented in the form of a prefabricated unit. The third band 39 is implemented analogously to the first and the second band 1, 2, wherein it is closable to form a ring by means of closure parts 4, 5. This ring is preferably located coaxially to the rings of the closed first and second bands 1, 2 (in the relaxed state of the device). The diameters of the discrete bands 1, 2, 39 in the closed and as yet unfilled state can be of equal size or they can differ. The elasticities of the inner walls 18 of the discrete bands 1, 2, 39 can be identical or they can differ. If the lengths of bands 1, 2, 39 and the elasticities of the inner walls 18 are equal, the passage openings 8 of bands 1, 2, 39 can be adjusted, for example, through separate injection ports. Valve means between the individual bands 1, 2, 39, analogously to the embodiment described in conjunction with FIG. 7, can also be provided. In the case of more than two bands, it is preferred if the passage openings of bands 1, 2, 39 decrease increasingly from proximal to distal—at least as long as there is no pressure acting on the bands due to supplied food.

The enveloping part 40 is connected with the second and third band 2, 39 analogously to the enveloping part 20 with the first and second band 1, 2 and is formed analogously to this enveloping part 20. Instead, a single continuous enveloping part could also be provided, which extends over the second band 2 on the outside of the same and is connected with all three bands 1, 2, 39, preferably in each case over substantially the entire circumference or at individual connection sites, which are spaced apart from one another, preferably by no more than 30°, in the circumferential direction.

Figure 11:
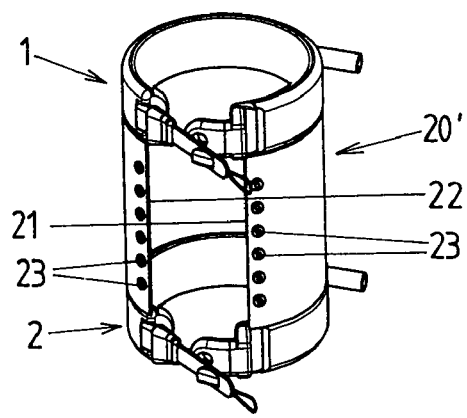
FIG. 11 is a further embodiment of the invention in the opened state of the bands, in oblique view, FIG. 12 a schematic diagram of a section of a band and of an enveloping part according to a further embodiment variant of the invention.

The embodiment example depicted in FIG. 11 differs from that depicted in FIG. 1 to 4 thereby that, instead of a mesh-like enveloping part 20 an enveloping part 20' formed by a film is provided. A silicon film is preferably utilized. In the region of the two circumferential ends, for example, suture eyelets 23 can be provided for the connection of the two circumferential ends 21, 22. A closure means, for example analogous to that depicted in FIG. 8, could also be provided. Such film-like enveloping parts 20' could also be utilized in the case of the other described embodiment examples. The film could also be provided with a multiplicity of punch-outs for the formation of penetration openings.

Figure 12:
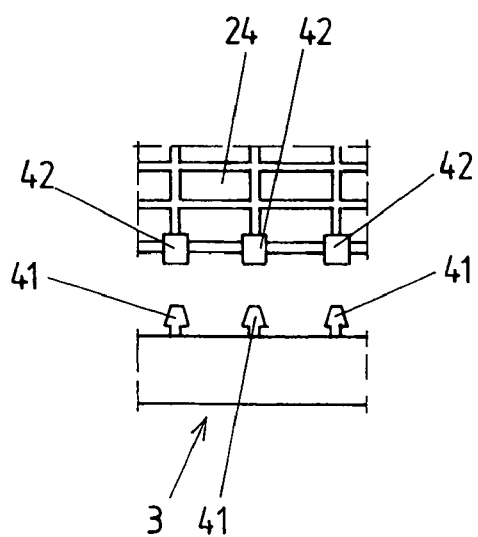

In the embodiment examples described so far the device according to the invention was in each instance formed as a unit prefabricated by the manufacturer, wherein the enveloping parts 20, 20', 40 are nondetachably connected with the bands 1, 2, 39. Instead, closure elements 41, 42 could, for example, also be provided in order to connect the enveloping part 20, 20', 40 in each instance with at least one of bands 1, 2, 39 or with each of the particular bands 1, 2, 39. Such an embodiment is depicted schematically and in sections in FIG. 12. The closure elements 41 including latch projections can herein be inserted into the eye-shaped closure elements 42 and be latched in position with them.

It would also be conceivable and feasible to suture the enveloping part 20, 20' 40 only after the placement of the bands 1, 2 39 with at least one of the bands 1, 2, 39 or with each particular band 1, 2, 39, which, however, is less preferred. Appropriate suture eyelets can be provided for this purpose.

Various further modifications of the described embodiments are conceivable and feasible without leaving the scope of the invention. For example, in the enveloping parts 20, 20', 40 window openings can be provided in order for tissue located outside of the enveloping parts (for example a folded-over section of the stomach wall) to be sutured to tissue located within the enveloping parts. Each of the bands 1, 2, 39 can also include several hollow chambers 15, as is known. Adjusting the cross section of each of the passage opening can also take place in a form other than through fillable hollow chambers, for example through piston-cylinder units, as is also known.

LEGEND TO THE REFERENCE NUMBERS

1 First band
2 Second band
3 Body section
4 First closure part
5 Second closure part
6 Extension
7 Latch projection
8 Passage opening
9 Draw tab
10 Prelatch projection
11 Suspension loop
12 Eye-shaped section
13 Draw tab
14 Opening
15 Hollow chamber
16 Connection tubule
17 Channel
18 Inner wall
19 Outer wall
20, 20' Enveloping part
21 Circumferential end
22 Circumferential end
23 Suture eyelet
24 Penetration opening
25 Injection port
26 Connection tubule
27 Connection tubule
28 Stomach
29 Esophagus
30 Connection tubule
31 Connection duct
32 Connection duct
33 Check valve
34 Spring element
35 Check valve
36 Spring element
37 First closure element
38 Second closure element
39 Third band
40 Enveloping part
41 Closure element
42 Closure element
43 Connection tubule

The invention claimed is:

1. Device for the treatment of obesity, comprising
a first band annularly placeable about the stomach with closure means for closing the band to form a ring,
a second band annularly placeable about the stomach with closure means for closing the band to form a ring, and
an enveloping part connected or connectable with the first and second band,
wherein the first band connected or connectable with the enveloping part can be placed about the esophagus, the stomach or a transition region between the esophagus and the stomach, and the second band, also connected or connectable with the enveloping part, is placeable about the stomach distally to the first band (1) and spaced apart from it, and the region of the stomach located between the first and the second band (1, 2) is envelopable by the enveloping part.

2. Device as claimed in claim 1, wherein the enveloping part is connected or is connectable substantially over the length of the first and of the second band continuously or at intervals with each of the particular band.

3. Device as claimed in claim 1 wherein the first and the second band and the enveloping part connected with the first and second band, are nondetachably connected with one another as a manufacturer's prefabricated unit.

4. Device as claimed in claim 3, wherein the enveloping part is adhered on the bands.

5. Device as claimed in claim 1, wherein the enveloping part is fastened or is fastenable by means of closure elements on the first or on the second band or on the first band and on the second band.

6. Device as claimed in claim 1, wherein the two circumferential ends of the enveloping part in the state of the device in which it is placed about the stomach, are adjacent to one another or sections of the enveloping part (20, 20') adjoining the two circumferential ends overlap one another and, for the formation of a circumferentially closed collar, the two adjacent circumferential ends or the overlapping sections adjoining the two circumferential ends are fastenable on one another.

7. Device as claimed in claim 6, wherein for the mutual fastening of the circumferential ends or of the overlapping sections of the enveloping part adjoining the circumferential ends these can be sutured to one another.

8. Device as claimed in claim 7, wherein for suturing the circumferential ends or the overlapping sections of the enveloping part adjoining the circumferential ends first and second rows of suture eyelets are provided.

9. Device as claimed in claim 6, wherein for the mutual fastening of the circumferential ends or of the overlapping sections of the enveloping part adjoining the circumferential ends a closure means is provided, which is preferably formed by closure elements that can be latched into position with one another.

10. Device as claimed in claim 1, wherein the first band includes at least one inner hollow chamber finable with a filler medium, which chamber extends at least over a large portion of the length of the first band, wherein through the filling of the hollow chamber the inner diameter of the ring formed by the closed first band can be decreased.

11. Device as claimed in claim 1, wherein the second band includes at least one inner hollow chamber fillable with a filler medium, which chamber extends at least over a large portion of the longitudinal extent of the second band, wherein through the filling of the hollow chamber the inner diameter of the ring formed by the closed second band can be decreased.

12. Device as claimed in claim 10, wherein the inner hollow chambers of the first and the second band are fillable by means of a common injection port.

13. Device as claimed in claim 12, wherein the inner hollow chambers of the first and the second band communicate freely with one another.

14. Device as claimed in claim 12, wherein the inner hollow chambers of the first and of the second band are connected with one another via a first and a second connection duct, wherein in the first connection duct a check valve is provided which is opened when a closure force for filler medium flowing from the first to the second band is exceeded, and in the second connection duct is provided a check valve which is opened when a closure force for filler medium flowing from the second to the first band is exceeded.

15. Device as claimed in claim 1, wherein the enveloping part is implemented in the form of a netting.

16. Device as claimed in claim 1, wherein the enveloping part is formed by a film.

17. Device as claimed in claim 1, wherein the enveloping part is comprised of silicon.

18. Device as claimed in claim 1, wherein the device comprises further a third band, annularly placeable about the stomach, distally to the second band and spaced apart from it, with closure means for closing the third band to form a ring, wherein the region of the stomach located between the second and the third band is envelopable by an enveloping part, extending over the second band up to the third band and connected and connectable with the third band, or by a further enveloping part connected or connectable with the second and the third band.

19. Device as claimed in claim 18, wherein the first, second and third band and the at least one enveloping part are non-detachably connected with one another as a manufacturer's prefabricated unit.

* * * * *